United States Patent
Scuri et al.

(10) Patent No.: US 10,098,837 B2
(45) Date of Patent: Oct. 16, 2018

(54) COMBINATION THERAPY FOR COPD

(71) Applicant: CHIESI FARMACEUTICI S.p.A., Parma (IT)

(72) Inventors: Mario Scuri, Parma (IT); Pierfrancesco Coli, Parma (IT); Giuseppe Delmonte, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/663,364

(22) Filed: Jul. 28, 2017

(65) Prior Publication Data

US 2018/0028439 A1   Feb. 1, 2018

Related U.S. Application Data

(60) Provisional application No. 62/367,894, filed on Jul. 28, 2016.

(30) Foreign Application Priority Data

Aug. 17, 2016  (EP) .................................. 16184608

(51) Int. Cl.
| | |
|---|---|
| *A61K 9/00* | (2006.01) |
| *A61K 31/56* | (2006.01) |
| *A61M 15/00* | (2006.01) |
| *A61K 47/02* | (2006.01) |
| *A61K 47/10* | (2017.01) |
| *A61K 31/167* | (2006.01) |
| *A61K 31/40* | (2006.01) |
| *A61K 31/573* | (2006.01) |
| *A61M 16/20* | (2006.01) |

(52) U.S. Cl.
CPC ............ *A61K 9/0075* (2013.01); *A61K 9/008* (2013.01); *A61K 31/167* (2013.01); *A61K 31/40* (2013.01); *A61K 31/56* (2013.01); *A61K 31/573* (2013.01); *A61K 47/02* (2013.01); *A61K 47/10* (2013.01); *A61M 15/0021* (2014.02); *A61M 15/0068* (2014.02); *A61K 9/00* (2013.01); *A61M 15/00* (2013.01); *A61M 16/20* (2013.01)

(58) Field of Classification Search
CPC ...... A61K 9/0075; A61K 9/008; A61K 31/56; A61K 9/00; A61M 15/0021; A61M 15/0068; A61M 15/00; A61M 16/20
USPC .......................................................... 514/385
See application file for complete search history.

(56) References Cited

U.S. PATENT DOCUMENTS

2015/0150787 A1  6/2015  Lechuga-Ballesteros et al.
2015/0182459 A1  7/2015  Bonelli et al.

FOREIGN PATENT DOCUMENTS

WO   2014/033057   3/2014

OTHER PUBLICATIONS

Extended European Search Report in Application No. 16184608.4 dated Sep. 30, 2016.
Singh Dave et al., Respiratory Medicine, Bailliere Tindall, London, GB, vol. 114, (2016) pp. 84-90.

*Primary Examiner* — Kristin Ann Vajda
(74) *Attorney, Agent, or Firm* — Oblon, McClelland, Maier & Neustadt, L.L.P.

(57) ABSTRACT

Aerosol formulations comprising glycopyrronium bromide, formoterol or a salt thereof, and beclometasone dipropionate are useful for the prevention or treatment of moderate/severe chronic obstructive pulmonary disease.

25 Claims, 4 Drawing Sheets

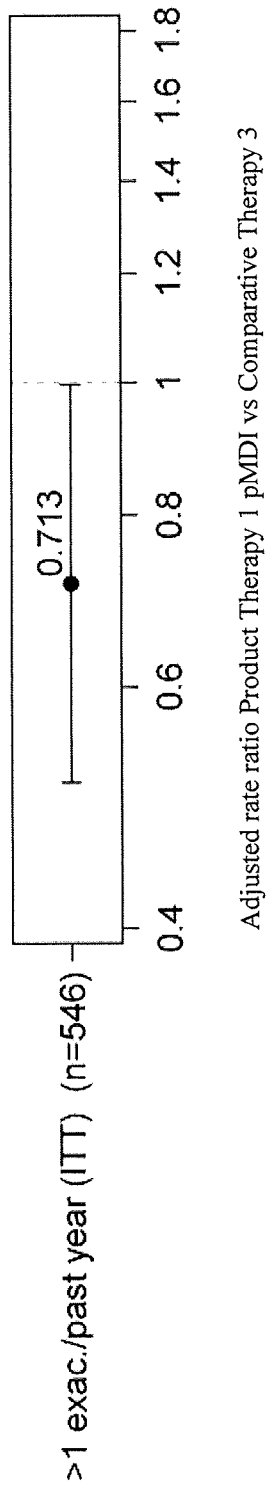
Figure 1: Moderate to severe COPD exacerbation rate reduction in the sub-group of patients with more than one exacerbation in the previous year of therapy after 52 weeks treatment with Product Therapy 1 pMDI according to the invention vs Comparative Therapy 3 (BDP+FF pMDI Plus tiotropium DPI) (ITT = Intention To Treat Analysis)

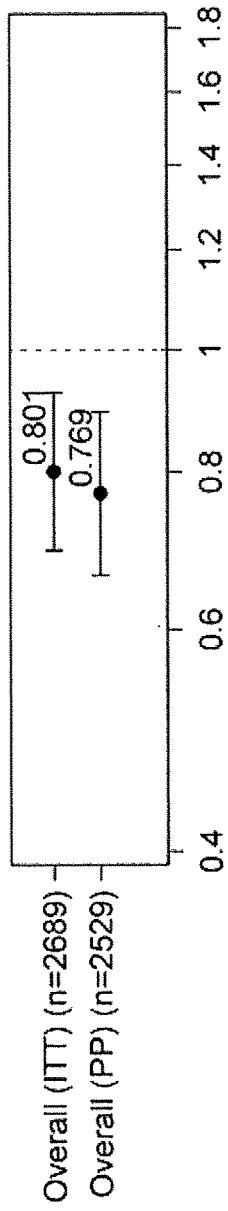

Figure 2: Moderate to severe COPD exacerbation rate reduction in the overall patients after 52 weeks treatment with Product Therapy 1 pMDI according to the invention vs Comparative Therapy 2 - tiotropium bromide DPI. (ITT = Intention-To-Treat Analysis; PP = Per-Protocol Analysis).

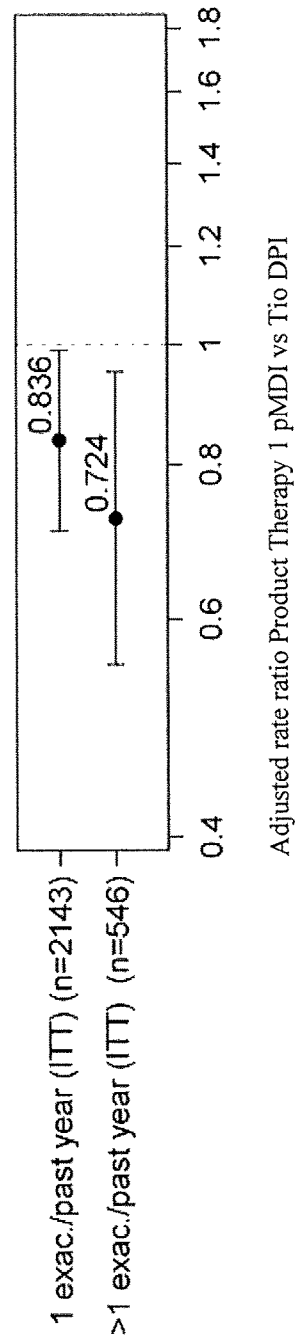

Figure 3: Moderate to severe COPD exacerbation rate reduction in the sub-groups of patients with one or more exacerbations in the previous year of therapy after 52 weeks treatment with Product Therapy 1 pMDI vs Comparative Therapy 2 -tiotropium bromide DPI (ITT = Intention To Treat Analysis).

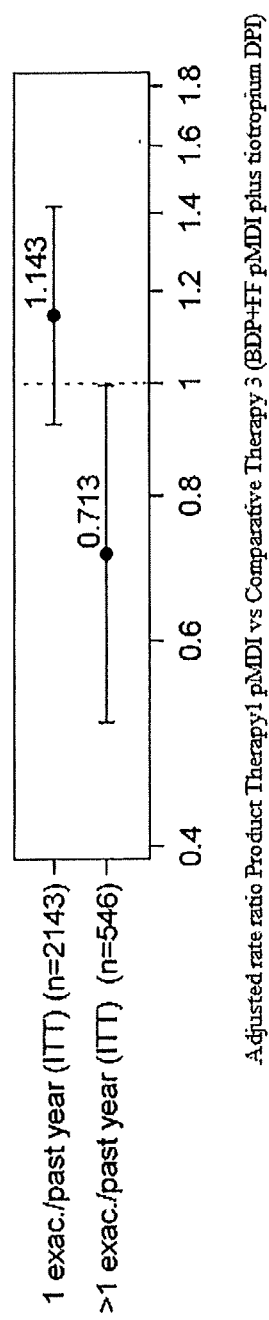
Figure 4A: Moderate to severe COPD exacerbation rate reduction, in the sub-groups of patients with one or more exacerbations in the year before the study entry, after 52 weeks treatment with Product Therapy 1 pMDI vs Comparative Therapy 3 (BDP+FF pMDI b.i.d. plus tiotropium bromide DPI once daily (ITT = Intention To Treat Analysis).

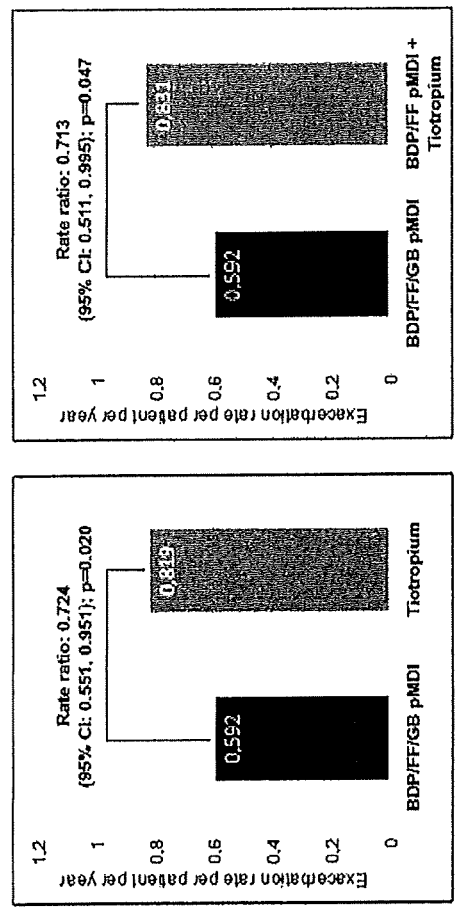
Figure 4B: Rate of moderate/severe exacerbations in COPD patients with more than 1 exacerbation the year before study entry for Product Therapy 1, Comparative Therapy (2), and Comparative Therapy (3).

COMBINATION THERAPY FOR COPD

CROSS REFERENCES TO RELATED APPLICATIONS

This application claims priority to U.S. Provisional Patent Application No. 62/367,894, filed on Jul. 28, 2016, and European Patent Application No. 16184608.4, filed on Aug. 17, 2016, both of which are incorporated herein by reference in their entireties.

BACKGROUND OF THE INVENTION

Field of the Invention

The present invention relates to methods for the prevention and therapy of respiratory disorders, including moderate/severe chronic obstructive pulmonary disease (COPD).

Discussion of the Background

Glycopyrronium bromide (also known as glycopyrrolate) is a long acting anti-muscarinic agent (LAMA), particularly active as an antagonist on the M3 sub-type cholinergic receptors, used to reduce salivation associated with administration of certain anaesthetics, and as adjunctive therapy for peptic ulcers. It has also been reported to be effective in the treatment of asthmatic symptoms (Hansel et al., Chest, 2005; 128:1974-1979, which is incorporated herein by reference in its entirety).

WO 2005/107873, which is incorporated herein by reference in its entirety, discloses the use of glycopyrrolate for the treatment of childhood asthma.

WO 01/76575, which is incorporated herein by reference in its entirety, discloses a controlled release formulation for pulmonary delivery of glycopyrrolate. The formulation is intended for use in treatment of respiratory disease, in particular chronic obstructive pulmonary disease (COPD). The application focuses on dry powder formulations suitable for delivery by means of a dry powder inhaler (DPI).

WO 2005/074918, which is incorporated herein by reference in its entirety, discloses combinations of glycopyrrolate with glucocorticoid drugs, and their use for treating diseases of the respiratory tract.

WO 2005/110402, which is incorporated herein by reference in its entirety, discloses combinations of glycopyrrolate and a long acting beta-2 agonist (LABA) of the class of indane or of benzothiazole-2-one derivatives for treatment of inflammatory or obstructive airway diseases.

WO 2006/105401, which is incorporated herein by reference in its entirety, discloses combinations of a LAMA, an inhaled corticosteroid (ICS) and a LABA for prevention and treatment of respiratory, inflammatory or obstructive airway diseases. The anticholinergic is optionally glycopyrrolate.

According to WO 2007/057223 and WO 2007/057222, both of which are incorporated herein by reference in their entireties, disclose combinations of glycopyrronium bromide respectively with an anti-inflammatory ICS and, in particular, with mometasone furoate provide a therapeutic benefit in the treatment of inflammatory and obstructive airways diseases.

WO 2007/057221 and WO 2007/057219, both of which are incorporated herein by reference in their entireties, disclose combinations of a glycopyrronium salt with an indanyl derivative LABA (or analogue) and respectively with an anti-inflammatory steroid and, in particular, with mometasone furoate.

Formoterol is a LABA that displays a rapid onset of action and capable of relaxing smooth muscle in the bronchi and opening the airways to reduce wheezing conditions. It is commonly used in the management of asthma and other respiratory conditions.

An effective combination therapy comprising formoterol fumarate and the ICS beclometasone dipropionate (BDP) has become available under the trade-name Foster®. Foster® is designed for delivery by aerosol to the lungs using a pressurized metered dose inhaler (pMDI). It has long been known that aerosol solutions of formoterol fumarate are relatively unstable and have a short shelf-life when stored under suboptimal conditions. The Foster® formulation incorporates a suitable amount of inorganic acid in order to stabilize the formoterol component (as described in EP 1 157 689, which is incorporated herein by reference in its entirety).

Dry powder inhalation (DPI) formulations of glycopyrronium bromide alone or in combination with the LABA indacaterol maleate have been approved and in the market for some years in the long term, maintenance treatment of airflow obstruction in patients with COPD. More recently also a pMDI co-suspension formulation of glycopyrronium bromide (10.4 µg per actuation) solid particles and formoterol fumarate (4.8 µg per actuation) solid particles with porous particles of 1,2-distearoyl-sn-glycero-3-phosphocholine (DSPC) and calcium chloride has been approved in the same indication.

US 2011/0150782, which is incorporated herein by reference in its entirety, discloses a stable pMDI solution formulation of a combination of glycopyrronium bromide, formoterol or a salt thereof, and beclometasone diproprionate (BDP).

US 2015/0182450 and US 2015/0182459, both of which are incorporated herein by reference in their entireties, disclose a pMDI solution formulation of a combination of glycopyrronium bromide, formoterol or a salt thereof, and BDP wherein the level of a specific degradation product, from the interaction between formoterol and glycopyrronium bromide is minimized after storage in particular container closure systems.

However, it would be desirable to provide a clinically useful aerosol product that combining in a single inhaler the therapeutic benefits of the bronchodilators formoterol and glycopyrronium bromide with the anti-inflammatory effect of beclometasone dipropionate is particularly effective for the treatment of moderate/severe COPD, especially in reducing the level of exacerbations in patients which were in therapy with a double inhalation therapy comprising ICS+LABA, ICS+LAMA and LABA+LAMA or with a single LAMA by inhalation which have experienced more than one exacerbation within the last year.

An exacerbation of COPD, as defined in Global Initiative for Chronic Obstructive Lung Disease (GOLD) Guideline (2015) is an acute event characterized by a worsening of the patient's respiratory symptoms that is beyond normal day-to-day variations and leads to a change in medication.

SUMMARY OF THE INVENTION

Accordingly, it is one object of the present invention to provide novel methods for the prevention and therapy of respiratory disorders.

It is another object of the present invention to provide novel methods for the prevention and therapy of respiratory disorders, including COPD.

It is another object of the present invention to provide novel methods for the prevention and therapy of respiratory disorders, including moderate/severe COPD.

It is another object of the present invention to provide novel methods for the prevention and therapy of respiratory disorders, including moderate/severe COPD in patients which have experienced more than one exacerbation within the last year.

It is another object of the present invention to provide pharmaceutical aerosol formulations for use in the prevention and treatment of respiratory disorders, including COPD and/or moderate/severe COPD particularly in patients that have experienced more than one exacerbation within the previous year.

These and other objects, which will become apparent during the following detailed description, have been achieved by the inventors' discovery that a pharmaceutical aerosol formulation comprising a fixed combination of:
 (a) glycopyrronium bromide;
 (b) formoterol or a salt or a solvate thereof; and
 (c) beclometasone dipropionate,
dissolved in hydrofluoroalkane (HFA) propellant and a co-solvent, wherein the formulation also comprises an inorganic acid as stabilizing agent, are useful for the prevention and therapy of respiratory disorders, including moderate/severe COPD in patients which have experienced more than one exacerbation within the last year.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the moderate to severe COPD exacerbation rate reduction in the sub-group of patients with more than one exacerbation in the previous year of therapy after 52 weeks treatment with Product Therapy 1 pMDI according to the invention vs Comparative Therapy 3 (BDP+FF pMDI Plus tiotropium DPI).

FIG. 2 shows the moderate to severe COPD exacerbation rate reduction in the overall patients after 52 weeks treatment with Product Therapy 1-pMDI according to the invention vs Comparative Therapy 2-tiotropium bromide DPI.

FIG. 3 shows the moderate to severe COPD exacerbation rate reduction in the sub-groups of patients with one or more exacerbations in the previous year of therapy after 52 weeks treatment with Product Therapy 1-pMDI vs Comparative Therapy 2-tiotropium bromide DPI.

FIG. 4A shows the moderate to severe COPD exacerbation rate reduction, in the sub-groups of patients with one or more exacerbations in the year before the study entry, after 52 weeks treatment with Product Therapy 1 pMDI vs Comparative Therapy 3 (BDP+FF pMDI b.i.d. plus tiotropium bromide DPI once daily FIG. 4B shows the rate of moderate to severe exacerbations in COPD patients with more than 1 exacerbations the year before study entry for Product Therapy 1, Comparative Therapy (2), and Comparative Therapy (3).

DETAILED DESCRIPTION OF THE PREFERRED EMBODIMENTS

Glycopyrronium bromide, chemically defined as 3-[(cyclopentylhydroxy-phenylacetyl)oxy]-1,1-dimethylpyrrolidinium bromide, has two chiral centers corresponding to four potential different stereoisomers with configurations (3R,2'R), (3S,2'R), (3R,2'S), and (3S,2'S). Glycopyrronium bromide in the form of any of these pure enantiomers or diastereomers or any combination thereof may be used in practising the present invention. In one embodiment of the present invention the (3S,2'R), (3R,2'S)-3-[(cyclopentylhydroxyphenylacetyl)oxy]-1,1-dimethylpyrrolidinium bromide racemic mixture, also known as glycopyrrolate, is preferred. Glycopyrronium bromide is present in the formulation in an amount in the range from 0.005 to 0.14% (w/w), preferably from 0.010 to 0.13% (w/w), more preferably from 0.015 to 0.04% (w/w), wherein % (w/w) means the amount by weight of the component, expressed as percent with respect to the total weight of the composition.

Glycopyrrolate is commercially available, and can be synthesized, for instance, according to the process described in U.S. Pat. No. 2,956,062 or in Franko B V and Lunsford C D, *J. Med. Pharm. Chem.*, 2(5), 523-540, 1960, both of which are incorporated herein by reference in their entireties.

Formoterol is a LABA which is prepared according to different methods well known in the art. Its molecule has two chiral centers and can be synthesised as four independent stereoisomers. Typically in the marketed products it is used the (R,R)-formoterol enantiomer or, more commonly, the racemic mixture of (R,R)- and (S,S)-formoterol. In the present invention we can include each of the individual enantiomeric form and their racemic mixtures as well. The preferred formoterol component of the formulation according to the invention is the (R,R)- and (S,S) racemic mixture of the free base, or a salt thereof, including those known in the art, or a solvate thereof. Preferably the formoterol salt is provided in the form of formoterol fumarate, and more preferably as its water solvate, known as formoterol fumarate dhydrate. Formoterol fumarate dihydrate can, for instance, be employed in the formulation in an amount of 0.005 to 0.07% w/w, preferably 0.01 to 0.02% w/w, wherein % (w/w) means the amount by weight of the component, expressed as percent with respect to the total weight of the composition.

The composition of the present invention also comprises the ICS beclometasone dipropionate (BDP) as active agent in addition to the formoterol fumarate and glycopyrronium bromide components. BDP, which can be prepared according to methods well known in the art, is preferably present in the formulation in an amount of 0.07 to 0.41% w/w, preferably 0.1 to 0.3% w/w, wherein % (w/w) means the amount by weight of the component, expressed as percent with respect to the total weight of the composition.

The propellant component of the composition may be any pressure-liquefied propellant and is preferably a hydrofluoroalkane (HFA) or a mixture of different HFAs, more preferably selected from the group consisting of HFA 134a (1,1,1,2-tetrafluoroethane), HFA 227 (1,1,1,2,3,3,3-heptafluoropropane), and mixtures thereof. The preferred HFA is HFA 134a. HFAs may be present in the formulation in an amount in the range from 75 to 95% (w/w), preferably from 85 to 90% (w/w), wherein % (w/w) means the amount by weight of the component, expressed as percent with respect to the total weight of the composition.

The co-solvent incorporated into formulations of the invention has a higher polarity than that of the propellant and may include one or more substances such as a pharmaceutically acceptable alcohol, in particular ethanol, or a polyol such as propylene glycol, polyethylene glycol or glycerol.

Advantageously the co-solvent is selected from the group of lower branched or linear alkyl ($C_1$-$C_4$) alcohols such as ethanol and isopropyl alcohol. Preferably the co-solvent is anhydrous ethanol.

The concentration of the co-solvent will vary depending on the final concentration of the active ingredient in the formulation and on the type of propellant. For example ethanol may be used in a concentration suitable to completely dissolve the active ingredients in the propellant and which is comprised in the range from 5 to 25% (w/w), preferably from 8 to 20% (w/w), more preferably from 10 to 15% (w/w), wherein % (w/w) means the amount by weight of the component, expressed as percent with respect to the total weight of the composition. In one of the preferred embodiments the concentration of ethanol is 12% (w/w).

The ratio of propellant to co-solvent in the formulation is in the range from 75:25 to 95:5 (w/w).

Further it is envisaged that the inorganic acid added to the formulation as a stabilizing agent is an amount of acid equivalent to from 0.1 to 0.6 µg/µl of formulation, preferably from 0.15 to 0.54 µg/µl of formulation, more preferably from 0.18 to 0.43 µg/µl of formulation, even more preferably 0.213 to 0.427 µg/µl of formulation, of 1M hydrochloric acid (HCl). Most preferably the amount of 1M HCl is selected from 0.213 µg/µl, 0.269 µg/µl, 0.427 µg/µl and 0.538 µg/µl of formulation.

HCl of different molarity or alternative inorganic acids (mineral acids) could substitute for 1M HCl in the formulations of the invention. Alternative acids may perhaps comprise pharmaceutically acceptable monoprotic or polyprotic acid, such as (but not limited to): hydrogen halides (hydrobromic acid, hydroiodic acid etc.) phosphoric acid, nitric acid, sulphuric acid, and halogen oxoacids.

The pharmaceutically active components of the composition are substantially completely and homogeneously dissolved in the mixture of propellant and co-solvent, i.e. the composition may thus be referred to a solution formulation.

Optionally, the solution formulation compositions may comprise other pharmaceutical excipients or additives known in the art. In particular, the compositions of the present invention may comprise one or more low volatility components. Low volatility components are useful in order to increase the mass median aerodynamic diameter (MMAD) of the aerosol particles upon actuation of the inhaler and/or to improve the solubility of the active ingredient in the propellant/co-solvent mixture.

The low volatility component, when present, has a vapor pressure at 25° C. lower than 0.1 kPa, preferably lower than 0.05 kPa. Examples of low-volatility components are esters such as isopropyl myristate, ascorbyl myristate, tocopherol esters; glycols such as propylene glycol, polyethylene glycol, glycerol; and surface active agents such as saturated organic carboxylic acids (e.g. lauric, myristic, stearic acid) or unsaturated carboxylic acids (e.g. oleic or ascorbic acid).

The amount of low volatility component, when present, may vary from 0.1 to 10% w/w, preferably from 0.5 to 5% (w/w), more preferably between 1 and 2% (w/w), wherein % (w/w) means the amount by weight of the component, expressed as percent with respect to the total weight of the composition.

In one embodiment the formulation lacks a low volatility component (e.g. isopropyl myristate) in order not to increase the MMAD of the aerosol particles upon actuation of the inhaler and/or not to improve the solubility of the active ingredient in the propellant/co-solvent mixture (e.g. where the MMAD of the aerosol particles and the solubility of the active ingredient is suitable in the absence of the low volatility component such as isopropyl myristate, typically where it is desirable to achieve a relatively low MMAD of the aerosol particles).

Advantageously, the formulations of the present invention are free of excipients (such as surfactants or low volatility components) other than co-solvent, propellant, and a stabilizing amount of an acid.

The compositions of the present invention can be inhaled from any suitable pressurized MDI device known to the skilled person. Desired doses of the individual pharmaceutically active components of the formulation are dependent on the identity of the component and the type and severity of the disease condition, but are preferably such that a therapeutic amount of the active ingredient is delivered in one or two actuations. Generally speaking, doses of active ingredient are in the range of about from 55 to 500 µg per actuation, e.g. about 58 to 450 µg per actuation, and in specific embodiments are selected from 59.25, 118.5, 218.5, 237 and 437 µg per actuation. The skilled person in the field is familiar with how to determine the appropriate dosage for each individual pharmaceutically active ingredient.

With reference to formoterol fumarate dihydrate, the preferred dosage is about 0.5 to 50 µs per actuation, preferably about 1 to 25 µg per actuation, and more preferably about 3 to 15 µg per actuation. In specific embodiments the dose of formoterol fumarate is 3, 6 or 12 µg per actuation.

With reference to glycopyrronium bromide, the preferred dosage is about 0.5 to 100 µg per actuation, preferably about 1 to 40 µg per actuation, and more preferably about 5 to 26 µg per actuation. In specific embodiments, the dose of glycopyrronium bromide is about 6.25, 12.5 or 25 µg per actuation.

With reference to beclometasone dipropionate, the preferred dosage is about 10 to 2000 µg per actuation, preferably about 20 to 1000 µg per actuation, and more preferably about 50 to 250 µg per actuation. In specific embodiments, the dose of beclometasone dipropionate is about 50, 100, 200 or 400 µg per actuation.

Therefore in an exemplary triple combination according to the invention the preferred dosage in µg/actuation of three active ingredients formoterol fumarate dihydrate/glycopyrronium bromide/BDP is selected respectively from the group of 3/6.25/50, 6/12.5/100, 6/12.5/200, 12/25/200 and 12/25/400.

The pharmaceutical formulation of the present invention is filled into pMDI devices known in the art. Said devices comprise a canister fitted with a metering valve. Actuation of the metering valve allows a small and precise portion of the spray product to be released.

Part, or all, of the canister may be made of a metal, for example aluminum, aluminum alloy, stainless steel or anodized aluminum. Alternatively the canister may be a plastic can or a plastic-coated glass container.

The metal canisters may have part or all of their internal surfaces lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene (FEP), polyether sulfone (PES) or fluorinated-ethylene-propylene polyether sulfone (FEP-PES) mixtures or combination thereof. Other suitable coatings could be polyamide, polyimide, polyamideimide, polyphenylene sulfide or their combinations.

In certain embodiments canisters having their internal surface lined with FEP, FEP-PES or Teflon may be used.

In a preferred embodiment, the composition is stored in an aluminum can which is internally coated by a resin comprising a resin comprising a fluorinated-ethylene-propylene (FEP) resin or a fluorinated-ethylene-propylene polyether sulfone (FEP-PES) resin, or a mixture or combination thereof.

Suitable cans are available from manufacturers such as, for instance, 3M, Presspart and Pressteck.

In other particular embodiments canisters made of stainless steel may be used.

The container is closed with a metering valve for delivering a daily therapeutically effective dose of the active ingredient. Generally, the metering valve assembly comprises a ferrule having an aperture formed therein, a body molding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise elastomeric material such as EPDM, chlorobutyl rubber, bromobutyl rubber, butyl rubber, or neoprene. EPDM rubbers are particularly preferred. The metering chamber, core, and core extension are manufactured using suitable materials such as stainless steel, polyesters (e.g. polybutyleneterephthalate (PBT)), or acetals. The spring is manufactured in stainless steel eventually including titanium. The ferrule may be made of a metal, for example aluminum, aluminum alloy, stainless steel or anodized aluminum. Suitable valves are available from manufacturers such as Valois, Bespak plc and 3M-Neotechnic Ltd.

In another preferred embodiment, the metering valve comprises at least a butyl rubber gasket. Among the butyl rubber, chlorobutyl rubber and bromobutyl rubber are preferred and chlorobutyl rubber is particularly preferred. The most preferred metering valve has all the seals made with the same elastomeric material which is selected from an EPDM elastomer or a butyl rubber and in particular butyl rubber is selected from a chlorobutyl or a bromobutyl rubber. Specific examples of such valves include butyl rubber valves from VARI, Rexam, and Coster and bromo-butylic valve Bespak (BK357).

The pMDI is actuated by a metering valve capable of delivering a volume of formulation of from 25 to 100 In preferred specific embodiments, the metering valve delivers a volume of about 25, 50, 63, or 100 μl per actuation.

In Table 1 the specific amount of 1M HCl required for the stabilization of a pMDI solution formulation of the fixed combination according to the invention, depending on the desired amounts of each active ingredient and on the metering valve volume used, is reported.

TABLE 1

Specific amount of 1M HCl to stabilize a pMDI solution formulation of the fixed combination in HFA 134a with 12% w/w ethanol depending on the desired amounts of each active ingredient and on the metering valve volume used.

| Formoterol fumarate dihydrate | Glycopyrronium bromide | BDP | Metering valve volume | 1M HCl | |
|---|---|---|---|---|---|
| (μg/act) | (μg/act) | (μg/act) | (μl) | (μg/μl) | (μl/act) |
| 3 | 6.25 | 50 | 25 | 0.269 | 6.72 |
| 6 | 12.5 | 100 | 25 | 0.538 | 13.44 |
| 6 | 12.5 | 100 | 50 | 0.269 | 13.44 |
| 6 | 12.5 | 100 | 63 | 0.213 | 13.44 |
| 6 | 12.5 | 200 | 63 | 0.213 | 13.44 |
| 12 | 25 | 200 | 63 | 0.427 | 26.88 |
| 12 | 25 | 400 | 100 | 0.269 | 26.88 |

In particular, for a fixed triple combination according to the invention, comprising formoterol fumarate dihydrate in the range of from 3 to 12 μg per actuation, an amount of 1M hydrochloric acid in the range of from 6.72 to 26.9 μg per actuation is required and preferably, for a fixed triple combination comprising 6 μg per actuation of formoterol fumarate dihydrate, 12.5 μs per actuation of glycopyrronium bromide and 100 μg per actuation of beclometasone dipropionate, the amount of 1M hydrochloric acid required is 13.449 μg per actuation.

Each filled canister is conveniently fitted into a suitable channelling device prior to use to form a metered dose inhaler for administration of the medicament into the lungs of a patient. Suitable channelling devices comprise, for example, a valve actuator and a cylindrical or cone-like passage through which medicament may be delivered from the filled canister via the metering valve to the mouth of a patient e.g. a mouthpiece actuator. In a typical arrangement, the valve stem is seated in a nozzle block which has an orifice leading to an expansion chamber. The expansion chamber has an exit orifice which extends into the mouthpiece. Actuator (exit) orifices having a diameter in the range 0.15 to 0.45 mm and a length from 0.30 to 1.7 mm are generally suitable. Preferably, an orifice having a diameter from 0.2 to 0.44 mm is used, e.g. 0.22, 0.25, 0.30, 0.33, or 0.42 mm.

In certain embodiments of the present invention, it may be useful to utilize actuator orifices having a diameter ranging from 0.10 to 0.22 mm, in particular from 0.12 to 0.18 mm, such as those described in WO 03/053501, which is incorporated herein by reference in its entirety. The use of said fine orifices may also increase the duration of the cloud generation and hence, may facilitate the coordination of the cloud generation with the slow inspiration of the patient.

To avoid the ingress of water into the formulation the MDI product may be overwrapped by a flexible package capable of resisting water ingress. It may also be desirable to incorporate a material within the packaging (e.g. a molecular sieve) which is able to adsorb any moisture entering into the canister or any propellant and co-solvent which may leak from the canister.

Optionally the MDI device filled with the formulation of the present invention may be utilized together with suitable auxiliary devices favoring the correct use of the inhaler. Said auxiliary devices are commercially available and, depending on their shape and size, are known as "spacers", "reservoirs" or "expansion chambers". Volumatic™ is, for instance, one of the most widely known and used reservoirs, while Aerochamber™ is one of the most widely used and known spacers. A suitable expansion chamber is reported for example in WO 01/49350, which is incorporated herein by reference in its entirety.

The formulation of the present invention may also be used with common pressurized breath-activated inhalers, such as those known with the registered names of Easi-Breathe™ and Autohaler™.

In addition the composition of the invention may be administered through an actuator provided with a mechanical or electronic dose counter or dose indicator known in the art which may be top-mounted externally to the actuator or integrated internally to the actuator. Such a dose counter or dose indicator may show, respectively, the number or the range of the doses administered and/or the number or the range of the doses remaining into the can.

The efficacy of an MDI device is a function of the dose deposited at the appropriate site in the lungs. Deposition is affected by the aerodynamic particle size distribution of the formulation which may be characterised in vitro through several parameters.

The aerodynamic particle size distribution of the formulation of the present invention may be characterized using a Cascade Impactor according to the procedure described in the European Pharmacopoeia 6th edition, 2009 (6.5), part 2.09.18. An Apparatus E, operating at a flow rate range of 30 l/minute to 100 l/minute or an Apparatus D—Andersen Cascade Impactor (ACI)—, operating at a flow rate of 28.3 l/minute, Deposition of the drug on each ACI plate is determined by high performance liquid chromatography (HPLC).

The following parameters of the particles emitted by a pressurized MDI may be determined:

i) mass median aerodynamic diameter (MMAD) is the diameter around which the mass aerodynamic diameters of the emitted particles are distributed equally;

ii) delivered dose is calculated from the cumulative deposition in the ACI, divided by the number of actuations per experiment;

iii) respirable dose (fine particle dose=FPD) is obtained from the deposition from Stages 3 (S3) to filter (AF) of the ACI, corresponding to particles of diameter ≤4.7 microns, divided by the number of actuations per experiment;

iv) respirable fraction (fine particle fraction=FPF) which is the percent ratio between the respirable dose and the delivered dose; and v) "superfine" dose is obtained from the deposition from Stages 6 (S6) to filter, corresponding to particles of diameter ≤1.1 microns, divided by the number of actuations per experiment.

The solutions of the present invention are capable of providing, upon actuation of the pMDI device in which they are contained, a total FPF higher than 40%, preferably higher than 50%, more preferably higher than 60%.

Moreover, the formulations of the present invention are capable of providing, upon actuation, a fraction higher than or equal to 30% of emitted particles of diameter equal to or less than 1.1 microns as defined by the content stages S6-AF of an Andersen Cascade Impactor, relative to the total fine particle dose collected in the stages S3-AF of the impactor. Preferably, the fraction of emitted particles of diameter equal to or less than 1.1 microns is higher than or equal to 40%, more preferably higher than 50%, even more preferably higher than 60%, most preferably higher than 70%.

According to a further aspect of the present invention there is provided a method of filling an aerosol inhaler with a composition of the present invention. Conventional bulk manufacturing methods and machinery well known to those skilled in the art of pharmaceutical aerosol manufacture may be employed for the preparation of large-scale batches for the commercial production of filled canisters.

A first method comprises:

a) preparing a solution of glycopyrronium bromide, formoterol fumarate, and beclometasone dipropionate in an optional co-solvent (e.g. ethanol), mineral acid, propellant comprising a HFA and optionally a low volatility component at a temperature from −50 to −60° C. at which the formulation does not vaporize;

b) cold-filling the inhaler with the prepared solution; and c) placing the valve onto the empty can and crimping.

An alternative method comprises:

a) preparing a solution of glycopyrronium bromide, formoterol fumarate, and beclometasone dipropionate in a co-solvent (e.g. ethanol), mineral acid, and optionally a low volatility component;

b) filling the open can with the bulk solution;

c) placing the valve onto the can and crimping; and d) pressure-filling the can with the I-WA propellant through the valve.

A further alternative method comprises:

a) preparing a solution of glycopyrronium bromide, formoterol fumarate, and beclometasone dipropionate and mineral acid in optional co-solvent (e.g. ethanol), optional low volatility component and HFA propellant using a pressurised vessel;

b) placing the valve onto the empty can and crimping; and c) pressure-filling the can with the final solution formulation through the valve.

In one embodiment of the present invention, oxygen is substantially removed from the headspace of the aerosol canister using conventional techniques in order to further stabilize the formoterol component, especially at higher acid concentrations. This can be achieved in different ways depending on the method of filling the container. Purging can be achieved by vacuum crimping or by using propellant, for instance. In a preferred embodiment, the second filling method described above is modified to incorporate an oxygen purge into step (c) by vacuum crimping.

The packaged formulations of the present invention are stable for extended periods of time when stored under normal conditions of temperature and humidity. In a preferred embodiment, the packaged formulations are stable for at least 6 months at 25° C. and 60% RH, more preferably for at least 1 year, most preferably for at least 2 years. Stability is assessed by measuring content of residual active ingredient. A "stable" formulation as defined herein means one retaining at least about 85%, preferably at least about 90%, and most preferably at least about 95% of residual content of each active ingredient at a given time point, as measured by HPLC-UV VIS.

The optimized stable formulations meet the specifications required by the ICH Guideline Q1B or CPMP/QWP/122/02 Rev.1, which is incorporated herein by reference in its entirety, relevant for drug product stability testing for the purposes of drug registration.

The combination product compositions of the present invention may be used for prophylactic purposes or therapeutic purposes or for symptomatic relief of a wide range of conditions, and in one aspect the invention therefore relates to use of any of these pharmaceutical compositions as a medicament. In particular, the combination products of the present invention are useful in the prevention or treatment of many respiratory disorders, such as asthma of all types and chronic obstructive pulmonary disease (COPD).

The present formulation in fixed combination is particularly effective for reducing the moderate/severe COPD exacerbation rate (for about 30%) in patients that were in inhalation therapy with a fixed or with a free (open) double combination of drugs belonging to the classes of ICS+LABA, ICS+LAMA, LABA+LAMA or with a single LAMA drug up to at least two months prior to screening and which have experienced more than one exacerbation in the previous year.

Thus the present invention provides a method for reducing the moderate/severe COPD exacerbation in a sub-group of patients with more than one exacerbation in the previous year of therapy, by administering to a subject in need thereof a therapeutically effective amount of an inhaled pharmaceutical composition comprising a fixed combination of:
(a) glycopyrronium bromide;
(b) formoterol or a solvate salt thereof; and
(c) beclometasone diproprionate,
all completely dissolved in a hydrofluoroalkane (HFA) propellant and a co-solvent, wherein the formulation also comprises an inorganic acid as stabilizing agent, wherein the moderate/severe COPD exacerbation rate is reduced by more than 20%, and in particular by about 29%, with respect to the inhalation therapy of an extemporaneous open triple combination of a single LAMA and of a fixed dose combination of a LABA+ICS.

In a preferred embodiment the invention provides a method for reducing the moderate/severe COPD exacerbation rate in a sub-group of patients with more than one exacerbation in the previous year of therapy, by administering to a subject in need thereof a therapeutically effective amount of an inhaled pharmaceutical composition comprising a fixed combination of:
(a) glycopyrronium bromide;
(b) formoterol or a solvate salt thereof; and
(c) beclometasone diproprionate,
all completely dissolved in a hydrofluoroalkane (HFA) propellant and a co-solvent, wherein the formulation also comprises an inorganic acid as stabilizing agent, wherein the moderate/severe COPD exacerbation rate is reduced by more than 20%, and in particular by about 29%, with respect to the inhalation therapy of an extemporaneous open triple combination of a single LAMA and of a fixed dose combination of a LABA+ICS wherein the single LAMA is tiotropium bromide.

In a more preferred embodiment the invention provides a method for reducing the moderate/severe COPD exacerbation rate in a sub-group of patients with more than one exacerbation in the previous year of therapy, by administering to a subject in need thereof a therapeutically effective amount of an inhaled pharmaceutical composition comprising a fixed combination of:
(a) glycopyrronium bromide;
(b) formoterol or a solvate salt thereof; and
(c) beclometasone diproprionate,
all completely dissolved in a hydrofluoroalkane (HFA) propellant and a co-solvent, wherein the formulation also comprises an inorganic acid as stabilizing agent, wherein the moderate/severe COPD exacerbation rate is reduced by more than 20%, and in particular by about 29%, with respect to the inhalation therapy of an extemporaneous open triple combination of a single LAMA and of a fixed dose combination of a LABA+ICS wherein the LABA is formoterol fumarate and the ICS is beclometasone dipropionate.

In an even more preferred embodiment the invention provides a method for reducing the moderate/severe COPD exacerbation rate in a sub-group of patients with more than one exacerbation in the previous year of therapy, by administering to a subject in need thereof a therapeutically effective amount of an inhaled pharmaceutical composition comprising a fixed combination of:
(a) glycopyrronium bromide;
(b) formoterol fumarate dihydrate; and
(c) beclometasone diproprionate,
all completely dissolved in HFA 134a propellant and a co-solvent, wherein the formulation also comprises 1M HCl as stabilizing agent, wherein the moderate/severe COPD exacerbation rate is reduced by more than 20%, and in particular by about 29%, with respect to the inhalation therapy of an extemporaneous open triple combination of a single LAMA and of a fixed dose combination of a LABA+ICS wherein the single LAMA is tiotropium bromide dry powder for inhalation (Spiriva Handihaler DPI) and the LABA+ICS is a formoterol fumarate+beclometasone dipropionate dissolved in a hydrofluoroalkane (HFA) propellant and a co-solvent wherein the formulation also comprises an inorganic acid as stabilizing agent (Foster pMDI).

Thus, in another aspect the invention relates to a pharmaceutical aerosol formulation for inhalation, comprising a fixed combination of:
(a) glycopyrronium bromide;
(b) formoterol or a salt thereof; and
(c) beclometasone diproprionate,
all completely dissolved in a hydrofluoroalkane (HFA) propellant and a co-solvent, wherein the formulation also comprises an inorganic acid as stabilizing agent, for use in reducing the moderate/severe COPD exacerbation rate of more than 20%, and in particular of about 29%, in a sub-group of patients with more than one exacerbation in the previous year of therapy, versus the inhalation therapy of an extemporaneous open triple combination of a single LAMA and of a fixed dose combination of a LABA+ICS.

In another preferred aspect the invention relates to a pharmaceutical aerosol formulation for inhalation, comprising a fixed combination of:
(a) glycopyrronium bromide;
(b) formoterol or a solvate salt thereof; and
(c) beclometasone diproprionate,
all completely dissolved in a hydrofluoroalkane (HFA) propellant and a co-solvent, wherein the formulation also comprises an inorganic acid as stabilizing agent, for use in reducing the moderate/severe COPD exacerbation rate of more than 20%, and in particular of about 29%, in a sub-group of patients with more than one exacerbation in the previous year of therapy, versus the inhalation therapy of an extemporaneous open triple combination of a single LAMA and of a fixed dose combination of a LABA+ICS wherein the single LAMA is tiotropium bromide.

In another more preferred aspect the invention relates to a pharmaceutical aerosol formulation for inhalation, comprising a fixed combination of:
(a) glycopyrronium bromide;
(b) formoterol or a solvate salt thereof; and
(c) beclometasone diproprionate,
all completely dissolved in a hydrofluoroalkane (HFA) propellant and a co-solvent, wherein the formulation also comprises an inorganic acid as stabilizing agent, for use in reducing the moderate/severe COPD exacerbation rate of more than 20%, and in particular of about 29%, in a sub-group of patients with more than one exacerbation in the previous year of therapy, versus the inhalation therapy of an extemporaneous open triple combination of a single LAMA and of a fixed dose combination of a LABA+ICS wherein the LABA is formoterol fumarate and the ICS is beclometasone dipropionate.

In another even more preferred aspect the invention relates to a pharmaceutical aerosol formulation for inhalation, comprising a fixed combination of:
(a) glycopyrronium bromide;
(b) formoterol fumarate dihydrate; and
(c) beclometasone diproprionate,
all completely dissolved in HFA 134a propellant and a co-solvent, wherein the formulation also comprises 1M HCl as stabilizing agent, for use in reducing the moderate/severe COPD exacerbation rate of more than 20%, and in particular of about 29%, in a sub-group of patients with more than one exacerbation in the previous year of therapy, versus the inhalation therapy of an extemporaneous open triple combination of a single LAMA and of a fixed dose combination of a LABA+ICS wherein the single LAMA is tiotropium bromide dry powder for inhalation (Spiriva Handihaler DPI) and the LABA+ICS is a formoterol fumarate+beclometasone dipropionate dissolved in a hydrofluoroalkane (HFA) propellant and a co-solvent wherein the formulation also comprises an inorganic acid as stabilizing agent (Foster pMDI).

The Global Initiative for Chronic Obstructive Lung Disease ("GOLD" 2015) defines:

mild COPD (GOLD 1) as being characterized by $FEV_1 \geq 80\%$ of predicted;

moderate COPD (GOLD 2) as being characterized by $50\% \leq FEV_1 \leq 80\%$ of predicted;

severe COPD (GOLD 3) as being characterized by $30\% \leq FEV_1 < 50\%$ of predicted; and very severe COPD (GOLD 4) as being characterized by $FEV_1 < 30\%$ of predicted.

$FEV_1$ is the forced expiratory volume in one second.

GOLD defines an exacerbation of COPD as an acute event characterized by a worsening of the patient's respiratory symptoms that is beyond normal day-to-day variations and leads to a change in medication.

Other features of the invention will become apparent in the course of the following descriptions of exemplary embodiments which are given for illustration of the invention and are not intended to be limiting thereof.

EXAMPLES

Example 1

Preparation of the Fixed Triple Combination Aerosol Solution Formulation

A composition of formoterol fumarate dihydrate (FF), beclometasone dipriopionate (BDP), and glycopyrronium bromide (GB) was prepared as shown in Table 2 and packaged in FEP coated aluminium cans provided with EPDM valves with a 63 µl metering chamber.

TABLE 2

Composition of the aerosol solution composition of the fixed triple combination of formoterol fumarate (FF) dihydrate, glycopyrronium bromide (GB) and beclometasone dipropionate (BDP). Content % w/w means the percent content by weight of each component with respect to the total weight of the composition

| Component | Mass in µg per actuation (63 µL) | Mass in µg/µL | Content % (w/w) |
|---|---|---|---|
| BDP | 100 | 1.59 | 0.135 |
| FF dihydrate | 6 | 0.095 | 0.0081 |
| GB | 12.5 | 0.20 | 0.0169 |
| Ethanol (anhydrous) | 8856 | 140.57 | 12.000 |
| 1M HCl | 13.44 | 0.213 | 0.0182 |
| HFA 134a | 64812 | 1028.76 | 87.82 |

Example 2

Comparison of the Administration of the Product (1) According to the Invention Against the Comparative Therapy (2) and the Comparative Therapy (3)

Product Therapy (1): it is the Fixed Dose pMDI Solution Formulation of the Example 1, consisting in a Triple combination of beclometasone dipropionate (BDP) 100 µg per actuation, formoterol fumarate (FF) dihydrate 6 µg per actuation, and glycopyrronium bromide (GB) 12.5 µg per actuation administered in two actuations bis in die (b.i.d.).

Comparative Therapy (2): it is a DPI Formulation of tiotropium bromide (Tio) 18 µg per actuation (Spiriva Handihaler) administered in one actuation once daily.

Comparative Therapy (3): it is an extemporaneous Triple combination of the Fixed Dose pMDI solution formulation of the double combination of BDP 100 µg per actuation and FF 6 µg per actuation in two actuations bis in die (b.i.d.) plus a DPI Formulation of tiotropium bromide 18 µg per actuation administered in one actuation once daily.

The efficacy of Product Therapy (1) was compared to that of Comparative Therapy (2) and to that of Comparative Therapy (3).

Patients were classified according to the Global Initiative for Chronic Obstructive Lung Disease (GOLD, 2014) classification scheme as symptomatic patients (CAT score ≥10) with high risk of airflow limitation, severe/very severe functional limitation and at high risk of developing an exacerbation (overall Classes C and D of GOLD classification) which are those with ≥2 exacerbations per year or with ≥1 exacerbation leading to hospitalization.

Main subjects baseline characteristics:

1. post salbutamol $FEV_1 < 50\%$ of the predicted normal value and $FEV_1/FVC < 0.7$;

2. a history of at least one exacerbation in the 12 preceding months; and 3. symptomatic patients having CAT score ≥10 (according to the COPD Assessment Test CAT (http://www.catestonline.org/) and BDI focal score ≤10 (Baseline Dyspnea Index according to Mahler D A et al. Chest 85, 751-758, 1984) were identified as being severe/very severe COPD patients.

A double-blind, double dummy, randomized, multinational, multicentre, 3-arm parallel-group, active-controlled study was conducted. The study included a one-week pre-screening period, a two-week run in period, and a 52-week treatment period. During the run-in period, the subjects received 18 µg of Tio DPI (Spiriva Handihaler) once daily, while during the treatment period, one group (Group 1) received two inhalations of Product Therapy (1) for a total daily dose of 400 µg of BDP, 24 µg of FF, and 50 µg of GB, another group (Group 2) received Comparative Therapy (2) for a total daily dose of 18 µg and the other group (Group 3) received Comparative Therapy (3) for a total daily dose of 400 µg of BDP, 24 µg of FF, and 18 µg of Tio.

The initial screening involved 3433 subjects, of which 2691 subjects were randomized into three groups, the Group 1 with 1078 subjects, Group 2 with 1075 subjects and Group 3 with 538 subjects. In Group 1 986 (91.5%) subjects completed the study, in Group 2 914 (85.0%) completed the study while in Group 3 496 (92.2%) subjects completed the study.

All the patients, up to two months prior to screening, were receiving a double inhalation therapy with ICS+LABA or ICS+LAMA or LABA+LAMA or with a single inhalation therapy with a LAMA.

The inhalation therapies performed by the patients up to two months prior to screening were all products normally in the market and consisting of double combinations or of single LAMA products including the active ingredients detailed in Table 3.

TABLE 3

Inhalation therapies followed by the patients up to two months prior to screening.

| Class | Drugs |
|---|---|
| ICS + LABA | Fixed combinations;<br>BDP + FORMOTEROL; BUDESONIDE + FORMOTEROL or FLUTICASONE + SALMETEROL<br>Free (open) combinations:<br>BDP, BUDESONIDE, CICLESONIDE or FLUTICASONE + FORMOTEROL, INDACATEROL or SALMETEROL |
| ICS + LAMA | BDP, BUDESONIDE, CICLESONIDE or FLUTICASONE + GLYCOPYRRONIUM BROMIDE or TIOTROPIUM |
| LABA + LAMA | FORMOTEROL, INDACATEROL or SALMETEROL + GLYCOPYRRONIUM BROMIDE or TIOTROPIUM |
| LAMA | GLYCOPYRRONIUM BROMIDE or TIOTROPIUM |

In Group 1 of patients treated with Product Therapy (1) according to the invention there was a statistically significant reduction of moderate/severe COPD exacerbation rate by about 20% compared to Group 2 (treated with Comparative Therapy 2) both in the overall patients and in the sub-group of patients which experienced one exacerbation in the previous year of therapy (see FIGS. 2 and 3). In Group 1 of patients there was also a statistically significant reduction of moderate/severe COPD exacerbation rate by about 28% compared to Group 2 (treated with Comparative Therapy 2) in patients which experienced more than 1 exacerbation in the previous year of therapy (see FIG. 2).

In Group 1 of patients treated with Product Therapy (1) according to the invention there was also a statistically significant and clinically relevant superiority in the reduction of the moderate/severe COPD exacerbation rate to about 30% compared to Group 3 (treated with Comparative Therapy 3) in the sub-group of patients with more than one exacerbation in the previous year of therapy (see FIG. 1).

The population with more than one exacerbation in the previous year of inhalation therapy is reported in Table 4 wherein for each treatment group (1, 2 or 3) are reported the number of patients and the kind of the previous therapy received up to two months prior to screening.

TABLE 4

Number of patients with more than one exacerbation in the previous year of therapy, belonging to the treatment groups 1, 2 and 3 and the kind of the previous therapy received up to two months prior to screening.

|  | Group 1<br>Prod.<br>Therapy 1<br>n.<br>(%) | Group 2<br>Comp.<br>Therapy 2<br>n.<br>(%) | Group 3<br>Comp.<br>Therapy 3<br>n.<br>(%) | Total |
|---|---|---|---|---|
| ICS/LABA | 161<br>(75.59) | 183<br>(79.57) | 78<br>(75.73) | 422 |
| ICS/LAMA | 7<br>(3.29) | 5<br>(2.17) | 5<br>(4.85) | 17 |
| LABA/LAMA | 19<br>(8.92) | 22<br>(9.57) | 12<br>(11.65) | 53 |
| LAMA | 26<br>(12.21) | 20<br>(8.70) | 8<br>(7.77) | 54 |
| Total | 213 | 230 | 103 | 546 |

The fixed dose triple pMDI combination of BDP+FF+GB b.i.d (Group 1, treated with Product Therapy 1) demonstrated a statistically significant superiority vs the LAMA monotherapy (Tio) DPI, once daily (Group 2, treated with Comparative Therapy 2) but, very surprisingly, Group 1 was also statistically significant superior even to an extemporaneous triple combination of the double combination of BDP+FF pMDI b.i.d plus Tio DPI once daily (Group 3, treated with Comparative Therapy 3).

As shown in FIGS. 4A and 4B, in the subgroups of patients with more than 1 exacerbations in the previous year, the reduction in the rate of moderate-to-severe exacerbations in Group 1 treated with Product Therapy (1) was larger when compared with Group 2 which received Comparative Therapy (2) and Group 3 which received Comparative Therapy (3) (see FIG. 4). Notably, the pMDI solution formulation of a fixed combination BDP/FF/GB in view of its performance in particle size distribution significantly reduced exacerbations by 29% compared to Group 3 which received Comparative Therapy (3) in the subgroup of patients with ≥2 exacerbations in the previous year (see FIG. 4).

For additional discussion, also see J. Vestbo, et al., "Single inhaler extrafine triple therapy versus long-acting muscarinic antagonist therapy for chronic obstructive pulmonary disease (TRINITY): a double-blind, parallel group, randomised controlled trial," The Lancet, vol. 389, No. 10082, pp. 1919-1929 (2017), and the Appendix, which is incorporated herein by reference in its entirety.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for reducing the moderate/severe COPD exacerbation rate in a sub-group of patients with more than one exacerbation in the previous year of therapy, by administering to a subject in need thereof a therapeutically effective amount of an inhaled pharmaceutical composition comprising a fixed combination of:
   (a) glycopyrronium bromide;
   (b) formoterol or a solvate salt thereof; and
   (c) beclometasone diproprionate,
   all completely dissolved in a hydrofluoroalkane (HFA) propellant and a co-solvent, wherein the inhaled pharmaceutical composition also comprises an inorganic acid as stabilizing agent, wherein the moderate/severe COPD exacerbation rate is reduced by more than 20%, with respect to the inhalation therapy of an extemporaneous open triple combination of a single LAMA and of a fixed dose combination of a LABA+ICS.

2. A method according to claim 1, wherein the moderate/severe COPD exacerbation rate is reduced by more than 20%, with respect to the inhalation therapy of an extemporaneous open triple combination of a single LAMA and of a fixed dose combination of a LABA+ICS wherein the single LAMA is tiotropium bromide.

3. A method according to claim 1, wherein the moderate/severe COPD exacerbation rate is reduced by more than 20%, with respect to the inhalation therapy of an extemporaneous open triple combination of a single LAMA and of a fixed dose combination of a LABA+ICS wherein the LABA is formoterol fumarate and the ICS is beclometasone dipropionate.

4. A method according to claim 2, wherein the moderate/severe COPD exacerbation rate is reduced by more than 20%, with respect to the inhalation therapy of an extemporaneous open triple combination of a single LAMA and of a fixed dose combination of a LABA+ICS wherein the single LAMA is tiotropium bromide dry powder for inhalation and the LABA+ICS is a formoterol fumarate+beclometasone dipropionate dissolved in a hydrofluoroalkane (HFA) propellant and a co-solvent wherein the formulation also comprises an inorganic acid as stabilizing agent.

5. A method according to claim 1, wherein the moderate/severe COPD exacerbation rate is reduced by 29%.

6. A method according to claim 1 for reducing the moderate/severe COPD exacerbation rate by administering an inhaled pharmaceutical composition consisting of a fixed combination of beclometasone dipropionate (BDP) 100 µg per actuation, formoterol fumarate (FF) dihydrate 6 µg per actuation and glycopyrronium bromide (GB) 12.5 µg per actuation completely dissolved in HFA 134a 87.82% w/w, anhydrous ethanol 12% w/w and 1M HCl 13.44 µg per actuation, administered in two actuations bis in die for reducing the moderate/severe COPD exacerbation rate of 29%, with respect to the inhalation therapy of an extemporaneous open triple combination of tiotropium bromide dry powder for inhalation 18 µg per actuation once daily and a fixed dose combination of FF dihydrate 6 µg per actuation+BDP dissolved in HFA 134a, anhydrous ethanol and stabilizing amount of 1M HCl in two actuations bis in die.

7. A method according to claim 1 wherein the sub-group of patients with more than one exacerbation in the previous year of therapy, were receiving up to two months prior to screening, a double inhalation therapy with ICS+LABA or ICS+LAMA or LABA+LAMA or a single inhalation therapy with a LAMA.

8. A method according to claim 1, wherein the sub-group of patients with more than one exacerbation in the previous year of therapy, were receiving up to two months prior to screening, a double inhalation therapy comprising:
a fixed combination of BDP+FORMOTEROL; BUDESONIDE+FORMOTEROL or FLUTICASONE+SALMETEROL or
a free (open) combination of BDP, BUDESONIDE, CICLESONIDE or FLUTICASONE plus FORMOTEROL, INDACATEROL or SALMETEROL or of
BDP, BUDESONIDE, CICLESONIDE or FLUTICASONE plus GLYCOPYRRONIUM BROMIDE or TIOTROPIUM
or of
FORMOTEROL, INDACATEROL or SALMETEROL plus GLYCOPYRRONIUM BROMIDE or TIOTROPIUM or
a single LAMA selected from GLYCOPYRRONIUM BROMIDE or TIOTROPIUM.

9. A method for treating moderate/severe COPD in a patient having experienced more than one exacerbation in the previous year of therapy, comprising administering to said patient a therapeutically effective amount of an inhaled pharmaceutical composition, comprising a fixed combination of:
(a) glycopyrronium bromide;
(b) formoterol or a solvate salt thereof; and
(c) beclometasone diproprionate,
all completely dissolved in a hydrofluoroalkane (HFA) propellant and a co-solvent, wherein said inhaled pharmaceutical composition further comprises an inorganic acid as a stabilizing agent.

10. The method of claim 1, wherein said sub-group of patients has had ≥2 exacerbations in the previous year of therapy.

11. The method of claim 9, wherein said sub-group of patients has had ≥2 exacerbations in the previous year of therapy.

12. The method of claim 1, wherein the pharmaceutical composition is a pharmaceutical composition for use with a pressurized metered dose inhaler, comprising:
(a) glycopyrronium bromide in an amount sufficient to deliver 5 to 26 µg per actuation;
(b) formoterol fumarate in an amount sufficient to deliver 3 to 15 µg per actuation; and
(c) beclometasone dipropionate in an amount sufficient to deliver 50 to 250 µg per actuation;
dissolved in HFA-134a and ethanol, wherein:
the composition comprises hydrochloric acid in an amount equivalent to 0.18 to 0.43 µg/µl of 1M HCl;
the composition comprises ethanol in an amount of 8 to 15% w/w of the composition; and
the composition comprises HFA-134a in an amount of 85 to 90% w/w of the composition.

13. The method of claim 12, wherein the formoterol fumarate is formoterol fumarate dihydrate.

14. The method of claim 12, wherein the glycopyrronium bromide is the racemic mixture (3S,2'R),(3R,2'S)-3-[(cyclopentylhydroxyphenylacetyl)oxy]-1,1-dimethylpyrrolidinium bromide.

15. The method of claim 12, wherein the pharmaceutical composition is free of excipients other than the ethanol, the HFA-134a, and the hydrochloric acid.

16. The method of claim 12, wherein the pharmaceutical composition is administered from a container that has been purged of oxygen.

17. The method of claim 12, wherein the pharmaceutical composition is administered from a container comprising a metering valve capable of delivering a volume of about 63 µl per actuation.

18. The method of claim 1, wherein the pharmaceutical composition comprises:
glycopyrronium bromide in an amount of 0.015 to 0.04% w/w of the composition;
formoterol fumarate in an amount of 0.005 to 0.07% w/w of the composition; and
beclometasone dipropionate in an amount of 0.07 to 0.41% w/w of the composition.

19. The method of claim 9, wherein the pharmaceutical composition is a pharmaceutical composition for use with a pressurized metered dose inhaler, comprising:
(a) glycopyrronium bromide in an amount sufficient to deliver 5 to 26 µg per actuation;
(b) formoterol fumarate in an amount sufficient to deliver 3 to 15 µg per actuation; and
(c) beclometasone dipropionate in an amount sufficient to deliver 50 to 250 µg per actuation;
dissolved in HFA-134a and ethanol, wherein:
the composition comprises hydrochloric acid in an amount equivalent to 0.18 to 0.43 µg/µl of 1M HCl;
the composition comprises ethanol in an amount of 8 to 15% w/w of the composition; and
the composition comprises HFA-134a in an amount of 85 to 90% w/w of the composition.

20. The method of claim 19, wherein the formoterol fumarate is formoterol fumarate dihydrate.

21. The method of claim 19, wherein the glycopyrronium bromide is the racemic mixture (3S,2′R),(3R,2′S)-3-[(cyclopentylhydroxyphenylacetyl)oxyl]-1,1-dimethylpyrrolidinium bromide.

22. The method of claim 19, wherein the pharmaceutical composition is free of excipients other than the ethanol, the HFA-134a, and the hydrochloric acid.

23. The method of claim 19, wherein the pharmaceutical composition is administered from a container that has been purged of oxygen.

24. The method of claim 19, wherein the pharmaceutical composition is administered from a container comprising a metering valve capable of delivering a volume of about 63 µl per actuation.

25. The method of claim 9, wherein the pharmaceutical composition comprises:
- glycopyrronium bromide in an amount of 0.015 to 0.04% w/w of the composition;
- formoterol fumarate in an amount of 0.005 to 0.07% w/w of the composition; and
- beclometasone dipropionate in an amount of 0.07 to 0.41% w/w of the composition.

* * * * *

UNITED STATES PATENT AND TRADEMARK OFFICE
CERTIFICATE OF CORRECTION

PATENT NO. : 10,098,837 B2
APPLICATION NO. : 15/663364
DATED : October 16, 2018
INVENTOR(S) : Mario Scuri et al.

Page 1 of 1

It is certified that error appears in the above-identified patent and that said Letters Patent is hereby corrected as shown below:

In the Specification

Column 13, Line 38, delete "dipriopionate" and insert -- dipropionate --,

In the Claims

Column 16, Line 49, Claim 1, delete "diproprionate," and insert -- dipropionate, --, Column 17, Line 67, Claim 9, delete "diproprionate," and insert -- dipropionate, --.

Signed and Sealed this
Twenty-sixth Day of May, 2020

Andrei Iancu
*Director of the United States Patent and Trademark Office*